United States Patent [19]
Cukjati

[11] Patent Number: 5,531,594
[45] Date of Patent: Jul. 2, 1996

[54] ORTHODONTIC JAW SCREW

[76] Inventor: Joseph F. Cukjati, 1916 Wendy St., Irving, Tex. 75060

[21] Appl. No.: 318,346

[22] Filed: Oct. 5, 1994

[51] Int. Cl.[6] ........................ A61D 5/00
[52] U.S. Cl. ........................ 433/1; 433/18
[58] Field of Search ................ 433/1, 2, 6, 18, 433/19, 24

[56] References Cited

U.S. PATENT DOCUMENTS

| | | | |
|---|---|---|---|
| 3,140,543 | 7/1964 | Menter | 433/1 |
| 3,798,773 | 3/1974 | Northcutt | 433/19 |
| 4,144,643 | 3/1979 | Krygier | 432/7 |
| 4,412,818 | 11/1983 | Thomson | 433/1 |
| 4,676,745 | 6/1987 | Zurita | 433/6 |
| 5,066,226 | 11/1991 | Summer | 433/19 |
| 5,151,027 | 9/1992 | Mann | 433/1 |
| 5,328,364 | 7/1994 | Doyle | 433/18 |

*Primary Examiner*—Nicholas D. Lucchesi
*Attorney, Agent, or Firm*—Cox & Smith Incorporated

[57] ABSTRACT

An apparatus for compressing the symphyseal area of the mandibular or maxillary of a mammal. This apparatus utilizes an adjustable jaw screw that permits the normal mastication of a ruptured symphyseal joint. The jaw screw, inserted into the mouth of the mammalian patient, has mounting members that conform to the contour of the forward jaw teeth of the patient. Adjusting the jaw screw compresses the mounting members against the forward jaw teeth thereby allowing the healing of the ruptured symphyseal joint.

4 Claims, 1 Drawing Sheet

ORTHODONTIC JAW SCREW

FIELD OF THE INVENTION

The invention relates, in general, to an orthodontic device for compression and retention of the mandibular or the maxillary symphyseal area of mammals. In particular, a device used for compression of alveolar bone fractures in the canine tooth area of feline and canine species. In greater particularity, the invention relates to a jaw screw attaching to forward jaw teeth of the upper or lower jaw of such species.

BACKGROUND OF THE INVENTION

The canine and feline species have a mandibular and maxillary symphyseal joint held together by interbony ligaments. Rupture of this union, mainly by trauma, causes separation of the interconnecting ligaments of the rami granulation. Applying external compression to the mandibular or maxillary during the healing process will facilitate the healing of the symphyseal joint. If compression is not applied to that joint, unwanted tissue grows between the torn ligamental ends causing in some cases a non-union of the joint. When this non-union occurs, normal mastication is difficult as each rami moves when chewing movements normally occur between the upper and lower jaws.

Orthodontic fixtures for mammals, in general, are well known in the art. An example of such a fixture is U.S. Pat. No. 5,151,027 to Mann. Mann discloses an orthodontic fixture useful in correcting lingual displacement of mandibular canine teeth of a mammal. The Mann patent satisfies the need for correcting buccal displacement of the canines' mandibular by moving the mandibular into its normal position where it will not traumatically interfere with the gingival tissue of the maxillar. However, this orthodontic fixture does not apply compression to the symphyseal area of either the mandibular or maxillary of a mammal.

U.S. Pat. No. 3,454,001 to Stockfisch discloses, a jaw screw used in jaw reconstruction. This jaw screw not only prevents normal use of the teeth while installed but also requires a plurality of adjusting screws to obtain the proper jaw line to jaw screw fit.

U.S. Pat. No. 4,573,914 to Nord discloses means for providing adjustable pressure between teeth in a fixed-type formative orthodontic appliance employed to increase dental arch size in a treatment plan to overcome crowding of the teeth.

Nord's orthodontic fixture is a fixed-type formative appliance and cannot provide compression to the symphyseal joint area.

The present invention will compress the symphyseal area of the mandibular or maxillary of a mammal, allowing the normal mastication of a ruptured joint. Also, the present invention produces a minimum discomfort to the mammalian patient.

SUMMARY OF THE INVENTION

The present invention is a veterinary adjustable jaw screw attaching to the crowns of the forward jaw teeth of a mammalian patient's mouth. This invention compresses the symphyseal area of the upper or the lower jaw to facilitate the healing process of this joined area following the rupture of that joint.

The present invention comprises a pair of upright, rigid, and symmetrically spaced mounting members each having a perforated tooth engaging surface. These mounting members are respectively contoured to abut the outer surface of the crowns of the forward jaw teeth. Those mounting members are secured to their respective teeth crowns by a dental adhesive applied to the teeth during installation of the jaw screw. The lower portions of those mounting members are axially attached to the opposite ends of two cylindrical tubes disposed in a telescopic and slidable relationship. A screw inserted into one end of one tube, threadably engages the second tube, thereby providing means for axially displacing the tubes. The axial displacement of the tubes compresses the upper or lower jaw symphyseal area of the mammalian patient.

If desired, a flat rectangular mounting member can be integrally attached to one of the tubes. This flat mounting member is sized to fit between the respective tooth crowns of the forward canine teeth and adjacent to the symphyseal area. Such flat mounting member securably attaches the jaw screw to the mandibular or maxillary providing additional retention to the upper or lower jaw of the patient.

Further advantages of this invention will be readily apparent to those skilled in the art from the following detailed description, taken in conjunction with the annexed sheets of drawings.

DETAILED DESCRIPTION OF THE PREFERRED EMBODIMENT

The orthodontic fixture disclosed and claimed herein is intended for use with any mammal that may benefit by utilizing this device. However, the primary recipients of the benefits of this device are canine or feline patients requiring veterinary dentistry.

Canine and feline species have a symphyseal joint that longitudinally bisects both the lower and upper jaws. Interbony ligaments hold those joints together by forming a union of two halves of either jaw. Rupture of this union causes trauma to the jaw area resulting from a variety of accidents involving animals. An example of this would be a dog or cat darting unexpectedly in front of an automobile, subsequently the automobile engages the dog or cat causing trauma and rupture of the symphyseal joint. This rupture separates the interconnecting ligaments of the rami granulation. During the healing process of symphyseal joint, tissue will grow between the torn ligamental ends of the ruptured ligaments causing a non-union of the this joint. Applying external compression to the jaw area during the healing process will result in normal mastication. However, if compression is not applied, normal mastication is difficult as each rami moves when chewing movements occur between the upper and lower jaw.

The present invention utilizes a jaw screw to apply external pressure to mandibular or maxillary during the healing process following the rupture of the respective symphyseal joint.

Figure 1:
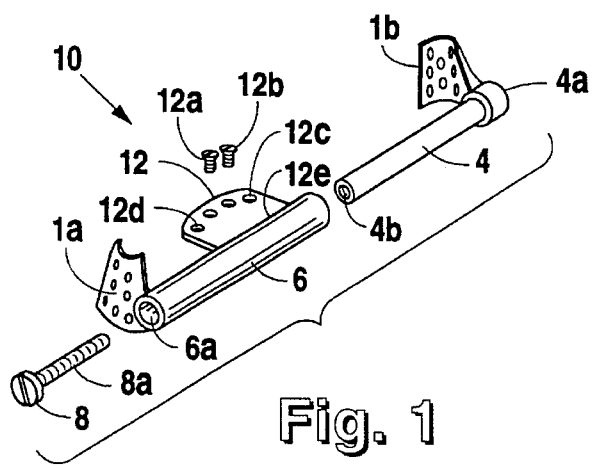
FIG. 1 is an exploded prospective view of a jaw screw embodying this invention.
Figure 2:
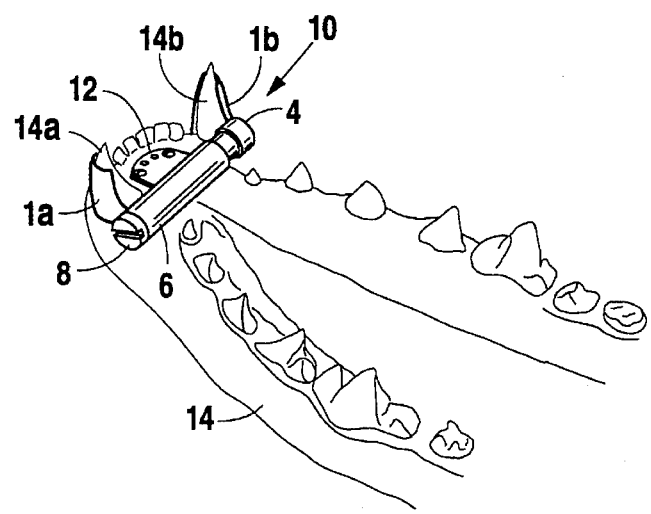
FIG. 2 is a perspective view of the jaw screw attached to the mandibular canines of a mammalian patient.

The drawings schematically illustrate an orthodontic jaw screw embodying this invention. FIG. 1 generally shows one embodiment of the present invention, jaw screw 10, in an exploded perspective view. Jaw screw 10 is attached to the proximal symmetrical crowns of the lower jaw 14 as shown in FIG. 2. Jaw screw 10 is not limited to the symmetrical spacing of the crowns and may, if desired, be attached to any two crowns disposed in either a lateral or adjacent relationship. This multi-placement of jaw-screw 10 would be the resultant of modifications to jaw-screw 10 that are within the scope of the present invention.

Jaw screw 10 further comprises a pair of upright mounting members 1a and 1b. These mounting members may, if desired, be made from steel, brass, or any suitable rigid material. Mounting members 1a and 1b each have a perforated surface contoured to fit the outer surface of the crowns 14a and 14b of the lower jaw 14 of the mammalian patient.

The present invention further comprises a first elongated rigid cylindrical tube 4 having at one end an outwardly projecting annular shoulder 4a for attaching the lower portion of upright mounting member 1b. A second elongated rigid cylindrical tube 6 has an inner bore 6a sized to receive tube 4's other end 4b. Tube end 4b is oppositely disposed from annular shoulder end 4a. Tube 4 is disposed in a telescopic and slidable relation with one end of tube 6. The other end of tube 6 has attached thereto the lower portion of upright mounting member 1a.

An adjusting screw 8 is inserted into tube 6 and engages tube end 4b. Tube end 4b is preferably internally threaded to receive screw 8. Adjusting screw 8 axially disposes mounting members 1a and 1b against crowns 14a and 14b of lower jaw 14.

A substantially flat rectangular mounting member 12 has its lower surface disposed adjacent to the symphyseal area of lower jaw 14 as shown in FIG. 2. Flat mounting member 12 has one long side 12e integrally attached along the longitudinal length of tube 6. Also, mounting member 12 has a plurality of laterally spaced holes 12d therethrough for receiving retaining screws 12a and 12b. Screws 12a and 12b secure jaw screw 10 to the lower jaw 14, preventing movement of jaw screw 10 when jaw screw 10 is inserted into the mouth of the mammalian patient.

Figure 3:
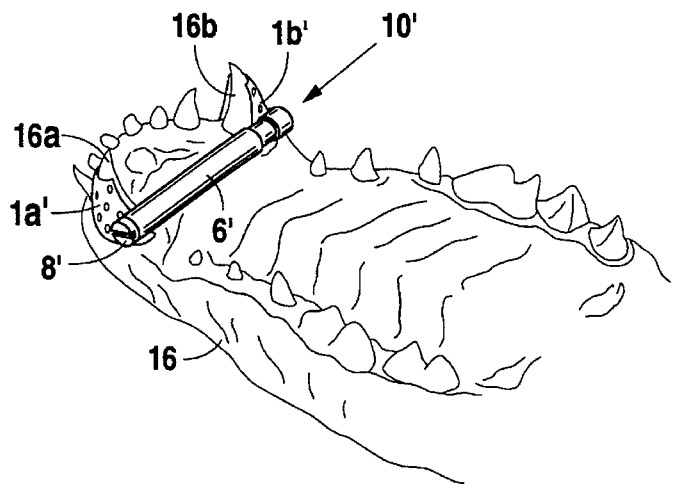
FIG. 3 is a perspective view of an alternate embodiment of the jaw screw of FIG. 1.

The preferred embodiment of the present invention is illustrated generally at 10' of FIG. 3. Jaw screw 10' comprises, generally, the same elements of jaw screw 10. That is upright mounting members 1a' and 1b', rigid cylindrical tubes 4' and 6'. and adjusting screw 8'. The functions of these elements are identical to the function of jaw screw 10.

Jaw screw 10' compresses the symphyseal area of upper jaw 16 without the aid of flat mounting member 12 of FIG. 1. Indeed, jaw screw 10' may, if desired, be used to compress the symphyseal area of lower jaw 14 if the medical condition of the patient warrants such a jaw screw. Conversely, jaw screw 10 with flat mounting member 12 may, if medical conditions warrant, attach to upper jaw 16 with no added discomfort to the mammalian patient.

Figure 4:
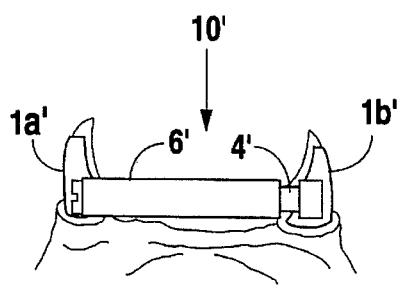
FIG. 4 is side elevation view of the jaw screw of FIG. 3.

FIG. 4 is a side elevational view of the jaw screw 10' attached to the proximal crowns of a mammalian patient. This view illustrates jaw screw 10' fully engaging the forward canine teeth of the upper or lower jaw of the mammalian patient.

Mounting members 1a, 1a', 1b, and 1b' may, if desired, be angled outwardly from their respective crowns to allow adhesive material to be more conveniently inserted therebetween. The adhesive material will provide additional support and retention of mounting members 1a, 1a', 1b, and 1b' to their respective crown surfaces. The adhesive material provided will flow through the perforated holes of mounting members 1a, 1a', 1b, and 1b' engaging the crown's surfaces, thereby bonding the crowns to their respective mounting members 1a, 1a', 1b, and 1b'.

The best mode of utilizing the present invention is to place jaw screw 10 into the mouth of an anesthetized mammalian patient requiring compression of the symphyseal area of lower jaw 14. Jaw screw 10 is secured to the crowns 14a and 14b of the forward canine teeth by adjusting screw 8 until mounting members 1a and 1b are in close proximity to the outer surface of crowns 14a and 14b. A measured amount of dental adhesive is placed between mounting members 1a and 1b and their respective crowns, then mounting members 1a and 1b are tightened against their respective crowns by adjusting screw 8. While the dental adhesive is solidifying screws' 12a and 12b are inserted into mounting member 12 and surgically disposed into the lower jaw 14 of the patient, thereby retaining jaw screw 10 to lower jaw 14.

The patient on occasion may rupture the symphyseal joint of upper jaw 16. If medical conditions warrant, jaw screw 10' may, if desired, be inserted into the mouth and retained therein by the same process disclosed above except that mounting member 12 is not attached to upper jaw 16.

The invention now being fully described, it will be apparent to one of ordinary skill in the art that many changes and modifications can be made thereto without departing from the spirit and scope of the invention as set forth herein.

I claim:

1. A veterinary adjustable jaw screw, attachable to the crowns of symmetrically spaced forward jaw teeth of a mammalian patient, for compressing and retaining the symphyseal area, comprising:

a pair of rigid symmetrically spaced mounting members respectively contoured to abut the outer surface of the crowns of the forward jaw teeth;

means for securing said mounting members to respective tooth crowns;

two rigid cylindrical tubes disposed in telescopic and slidable relation, each said tube having one end integrally connected to one of said mounting members;

means for axially displacing said tubes towards each other thereby compressing and retaining the symphyseal area;

a substantially flat rectangular mounting member having one surface disposed adjacent to the symphyseal area when installed in a patient and said flat mounting member having one long side integrally attached along the longitudinal length of one said tube; and means for securing said flat mounting member to the symphyseal area.

2. An adjustable jaw screw as recited in claim 1, wherein said means for axially displacing said mounting members comprises, an adjusting screw inserted into one end of one of said tubes and threadably engaging the other said tube, whereby said screw adjustably secures said mounting members to their respectively engaging tooth crowns.

3. A veterinary adjustable jaw screw, attachable to the crowns of the symmetrically, spaced forward jaw teeth of a mammal, for compressing and retaining the maxillary symphyseal area, comprising:

a pair of upright rigid mounting members each having a perforated surface respectively contoured to abut the outer surface of the crowns of the forward jaw teeth;

a first elongated, rigid cylindrical tube having at one end an outwardly projecting annular shoulder for attaching the lower portion of one said upright mounting member;

a second elongated, rigid cylindrical tube having an inner bore in one end sized to receive said first tubes other end;

said first tube being disposed in telescopic and slidable relation with said second tube;

said second tube's other end having attached thereto the lower portion of said other upright mounting member;

an adjusting screw inserted into one end of said second tube and engaging said first tube's other end opposite said shoulder, whereby said screw adjustably secures said upright mounting members to their respectively engaging tooth crowns;

a substantially flat rectangular mounting member having one surface disposed adjacent to the maxillary symphyseal area when installed in a patient and said flat mounting member having one long side integrally attached along the longitudinal length of one of said tubes; and means for securing said flat mounting member to the maxillary symphyseal area.

4. A veterinary adjustable jaw screw for compressing a longitudinal rupture in the symphyseal area of the jaw of a mammal having teeth disposed in the jaw on opposite sides of the rupture; comprising:

a pair of rigid mounting members respectively contoured to fit the outer surfaces of the crowns of two of said teeth on opposite sides of the rupture;

said rigid mounting members each comprising a plate element having perforations therein and respectively contoured to abut said outer surfaces of said crowns;

an adhesive filling said perforations and adapted to rigidly secure said mounting members to said crowns;

two rigid cylindrical tubes disposed in telescopic relation, each said tube having one end rigidly connected to one of said mounting members; and means for axially displacing said tubes toward each other, thereby compressing said rupture in the symphyseal area.

* * * * *